US009260497B2

(12) United States Patent
Kim et al.

(10) Patent No.: US 9,260,497 B2
(45) Date of Patent: Feb. 16, 2016

(54) USE OF MUTANT HAPTOGLOBIN HAVING ANGIOGENESIS PROMOTING ACTIVITY

(71) Applicant: CATHOLIC UNIVERSITY INDUSTRY ACADEMIC COOPERATION FOUNDATION, Seoul (KR)

(72) Inventors: In-Sook Kim, Seoul (KR); Mi-Kyung Oh, Seoul (KR)

(73) Assignee: CATHOLIC UNIVERISTY INDUSTRY ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 14/761,157

(22) PCT Filed: Aug. 20, 2013

(86) PCT No.: PCT/KR2013/007472
§ 371 (c)(1),
(2) Date: Jul. 15, 2015

(87) PCT Pub. No.: WO2014/112702
PCT Pub. Date: Jul. 24, 2014

(65) Prior Publication Data
US 2016/0017013 A1    Jan. 21, 2016

(30) Foreign Application Priority Data

Jan. 15, 2013   (KR) ........................ 10-2013-0004209

(51) Int. Cl.
*C07K 14/47* (2006.01)
*A61K 38/00* (2006.01)

(52) U.S. Cl.
CPC ............. *C07K 14/4717* (2013.01); *A61K 38/00* (2013.01)

(58) Field of Classification Search
None
See application file for complete search history.

(56) References Cited

FOREIGN PATENT DOCUMENTS

KR       2011-0102788 A     9/2011

OTHER PUBLICATIONS

Cid et al., "Identification of haptoglobin as an angiogenic factor in sera from patients with systemic vasculitis", The Journal of Clinical Investigation, vol. 91, No. 3, Mar. 1993, pp. 977-985.
Jiang et al., "Angiogenesis by transplantation of HIF-1 modified EPCs into ischemic limbs", Journal of Cellular Biochemistry, vol. 103, 2008, pp. 321-334.
Lim et al., "Haptoglobin reduces renal oxidative DNA and tissue damage during phenylhydrazine-induced hemolysis", Kidney International, vol. 58, Issue 3, Sep. 2000, pp. 1033-1044.
De Kleijn, "Acute-phase protein haptoglobin is a cell migration factor involved in arterial restructuring", FASEB Journal, vol. 16, Jul. 2002, pp. 1123-1125.
Lohr et al., "Haptoglobin expression and activity during coronary collateralization", American Journal of Physiology—Heart and Circulatory Physiology, vol. 288, No. 3, Mar. 1, 2005, pp. H1389-H1395.
Yang, et al., "Identification and characterization of human haptoglobin cDNA", Proceedings of the National Academy of Sciences, vol. 80, No. 19, Oct. 1983, pp. 5875-5879.
Park, et al., "The role of haptoglobin on proliferation and differentiation of endothelial progenitor cells", Department of Natural Sciences, Korean Society for Biochemistry and Molecular Biology, KSBMB, Abstract of 1991 19th FAOBMB Seoul Conference, Poster Session, vol. 2007, p. 432.
Carmeliet, Mechanisms of angiogenesis and arteriogenesis, Nature Medicine, vol. 6, No. 3, Mar. 2000, pp. 572-579.
Asahara, "Endothelial progenitor cells for postnatal vasculogenesis", American Journal of Physiology—Cell Physiology, vol. 287, No. 3, Sep. 1, 2004, pp. 389-396.
Jackson et al., "The codependence of angiogenesis and chronic inflammation", FASEB Journal, vol. 11, 1997, pp. 457-465.
Wilson et al., "Hepatocyte-directed gene transfer in vivo leads to transient improvement of hypercholesterolemia in low density lipoprotein receptor-deficient rabbits", Journal of Biological Chemistry, vol. 267, No. 2, 1992, pp. 963-967.
Jujo et al., "Endothelial progenitor cells in neovascularization of infarcted myocardium", Journal of Molecular and Cellular Cardiology, vol. 45 (2008), pp. 530-544.
Urbich et al., "Soluble factors released by endothelial progenitor cells promote migration of endothelial cells and cardiac resident progenitor cells", Journal of Molecular and Cellular Cardiology, vol. 39, Issue 5, Nov. 2005, pp. 733-742.
Smeets et al., "Nitric oxide synthesis is involved in arterial haptoglobin expression after sustained flow changes", FEBS Letters, vol. 529, 2002, pp. 221-224.
Brooks, "Role of integrins in angiogenesis", European Journal of Cancer, vol. 32A, No. 14, 1996, pp. 2423-2429.
Hananan et al., "Patterns and Emerging Mechanisms of the Angiogenic Switch during Tumorigenesis", Cell, vol. 86, 1996, pp. 353-364.
Wu et al., "Receptor-mediated gene delivery and expression in vivo", Journal of Biological Chemistry, vol. 263, No. 29, 1988, pp. 14621-14624.
Folkman et al., "Angiogenesis", The Journal of Biological Chemistry, vol. 267, No. 16, 1992, pp. 10931-10934.

(Continued)

*Primary Examiner* — Suzanne M Noakes
(74) *Attorney, Agent, or Firm* — Carter, DeLuca, Farrell & Schmidt, LLP

(57) ABSTRACT

The present invention relates to a use of mutant haptoglobin having angiogenesis-promoting activity and, more particularly, to a mutant haptoglobin polypeptide, a recombinant vector containing a polynucleotide encoding the polypeptide, or a composition for promoting angiogenesis containing, as an active ingredient, a transformant transformed with the recombinant vector. The mutant haptoglobin according to the present invention includes an amino acid sequence of SEQ ID NO: 1 in which the 143rd amino acid is substituted with an amino acid other than Arg. The mutant haptoglobin according to the present invention has excellent angiogenesis-promoting activity and excellent capillary-like tube formation capability as compared with wild-type haptoglobin, and promotes cell migration, and thus is useful as a therapeutic agent for treating diseases caused by non-angiogenesis.

10 Claims, 12 Drawing Sheets

(56) References Cited

OTHER PUBLICATIONS

Risau, "Mechanisms of angiogenesis", Nature, vol. 386, 1997, pp. 671-674.

Iwaguro et al., "Endothelial progenitor cell vascular endothelial growth factor gene transfer for vascular regeneration", Circulation, vol. 105, 2002, pp. 732-738.

Bussolino et al., "Molecular mechanisms of blood vessel formation", Trends in Biochemical Sciences, vol. 22, 1997, pp. 251-256.

Maeda et al., "Duplication within the haptopglobin Hp2 gene", Nature, vol. 309, 1984, pp. 131-135.

Buehler et al., "Haptoglobin preserves the CD163 hemoglobin scavenger pathway by shielding hemoglobin from peroxidative modification", Blood, vol. 113, 2009, pp. 2578-2586.

Folkman, "Angiogenesis in cancer", vascular, rheumatoid and other disease, Journal of Natural Medicines, vol. 1, 1995, pp. 27-31.

International Search Report issued in corresponding application No. PCT/KR2013/007472 on Nov. 19, 2013.

FIG. 1

α-chain

```
1                    10                   20                        30
V D S G N D V T D I A D D G C P K P P E I A H G Y V E H S V
                     40                   50                        60
R Y Q C K N Y Y K L R T E G D G V Y T L N D K K Q W I N K A
                     70                   80                        90
V G D K L P E C E A D D G C P K P P E I A H G Y V E H S V R
                     100                  110                       120
Y Q C K N Y Y K L R T E G D G V Y T L N N E K Q W I N K A V
                     130                                  142    1
G D K L P E C E A Y C G K P K N P A N P V Q         I L G G H L D
```

β-chain

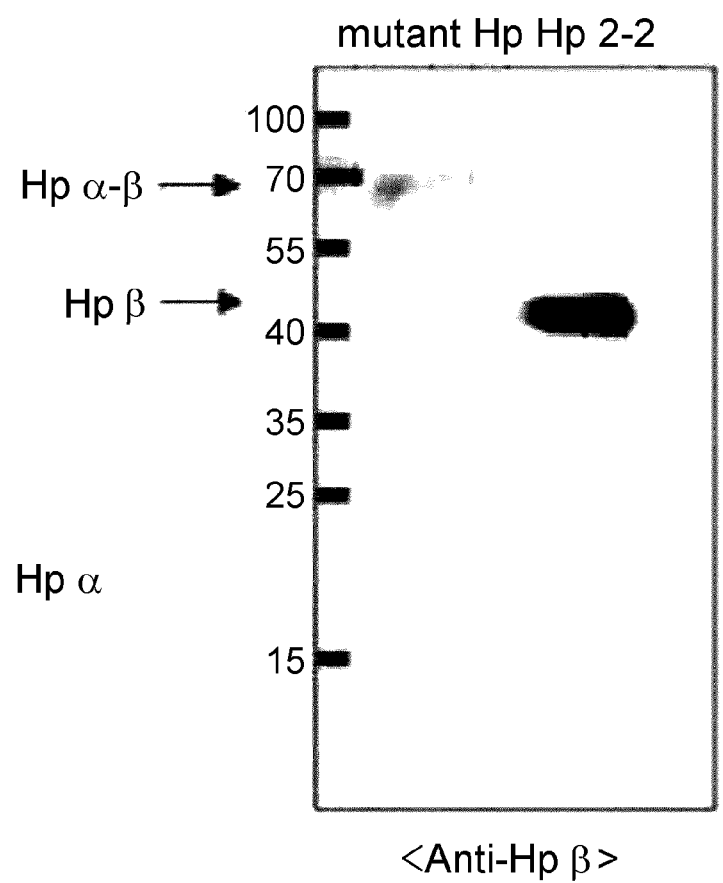

FIG. 5a
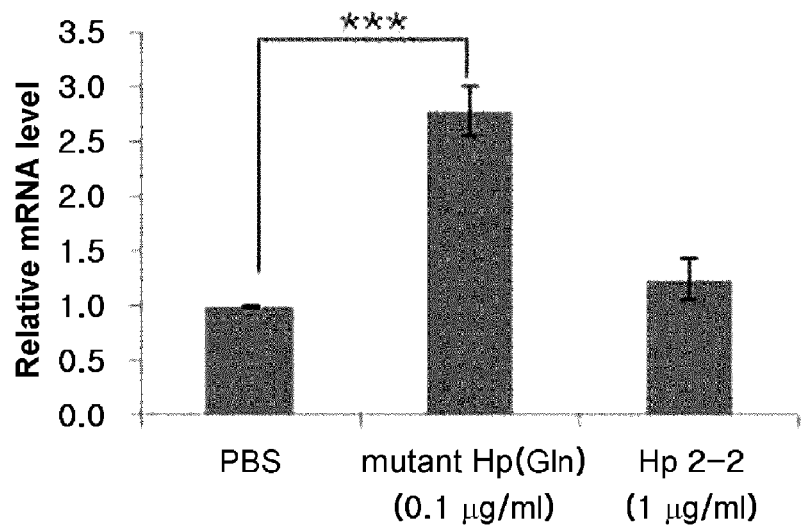
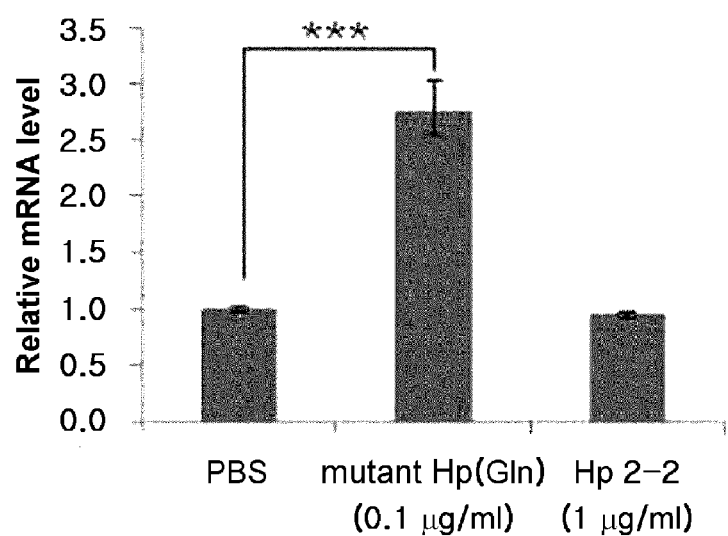

FIG. 5b
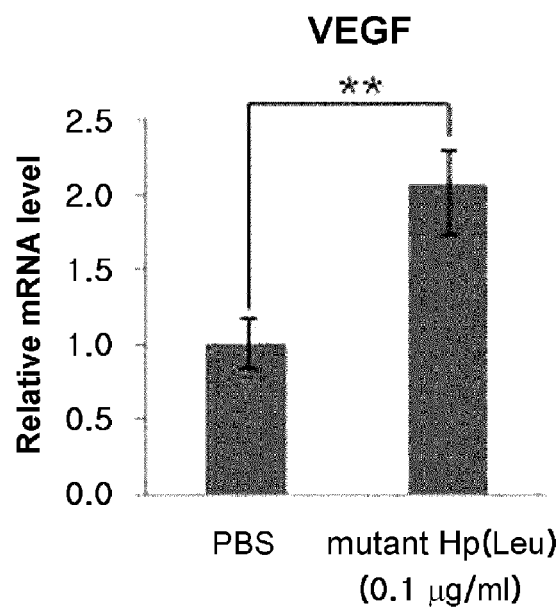
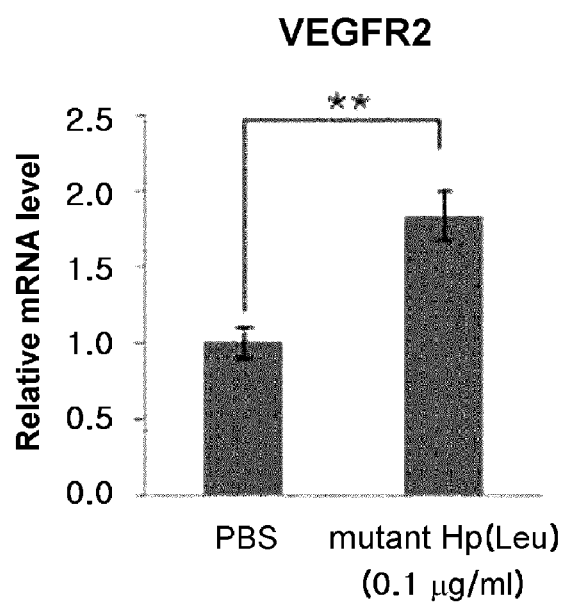

FIG. 6
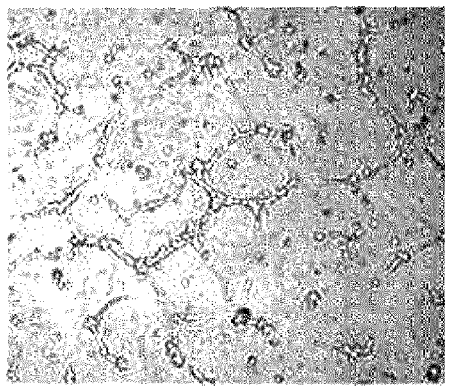
PBS
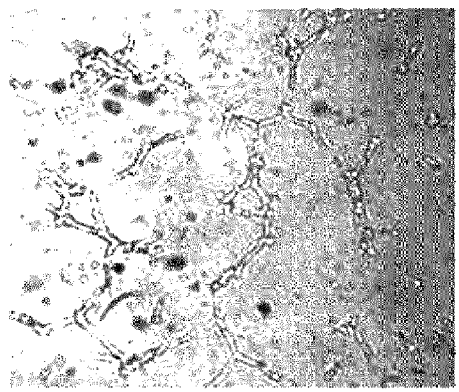
PBS
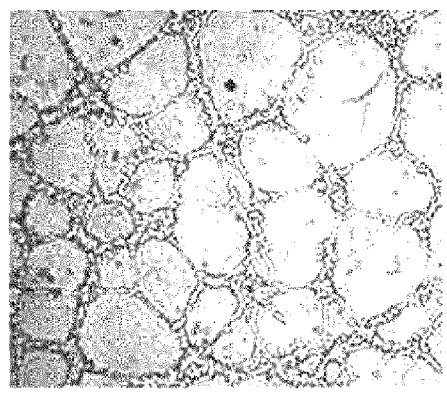
mutant Hp(Gln) (0.1 μg/ml)
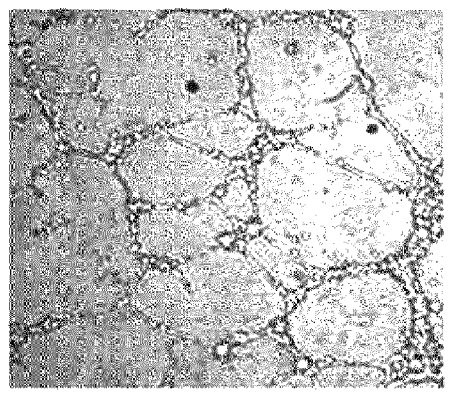
mutant Hp(Leu) (0.1 μg/ml)
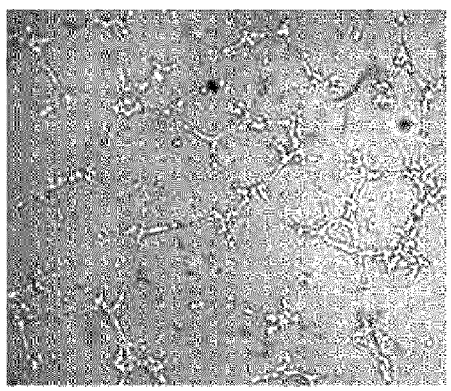
Hp 2-2 (1 μg/ml)
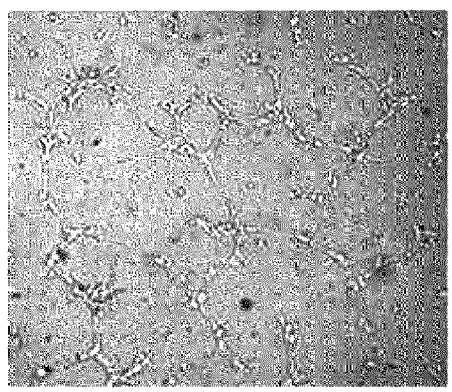
Hp 2-2 (1 μg/ml)

FIG. 7a
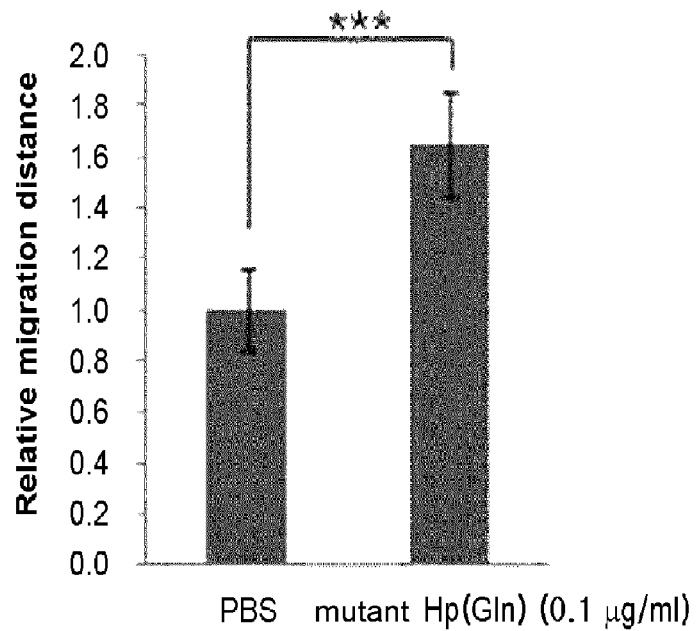
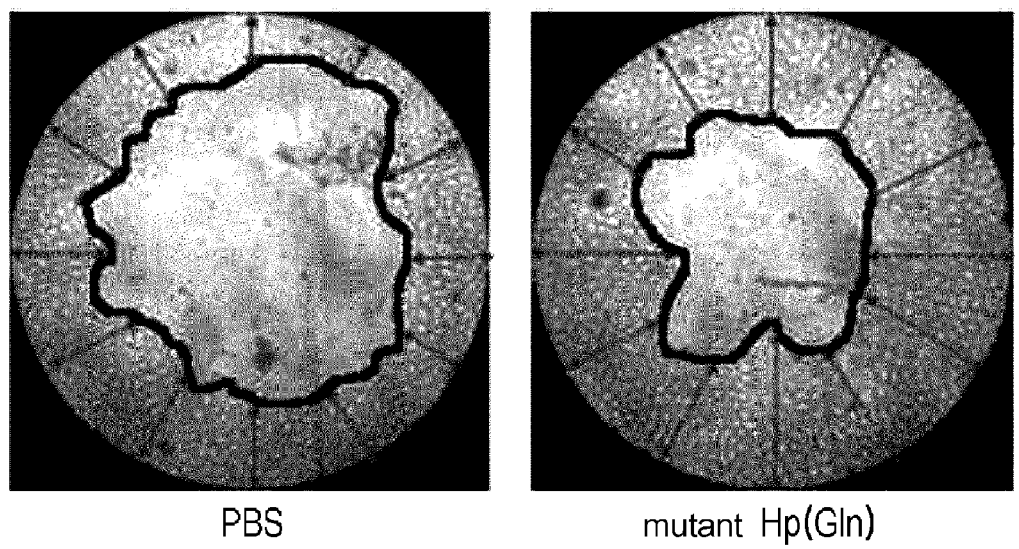

FIG. 7b
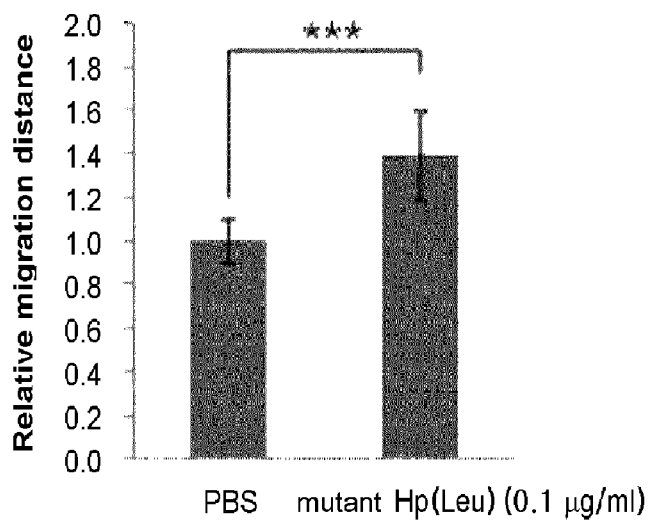
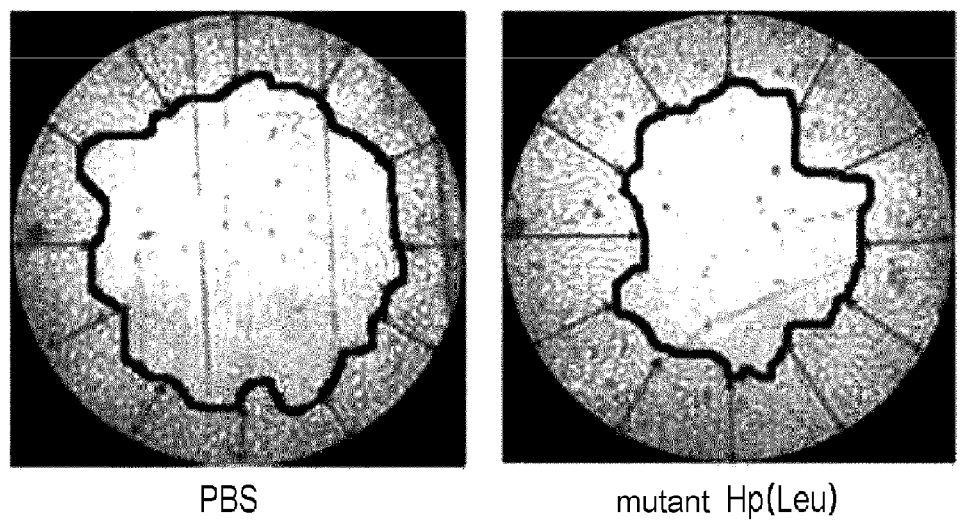

FIG. 7c
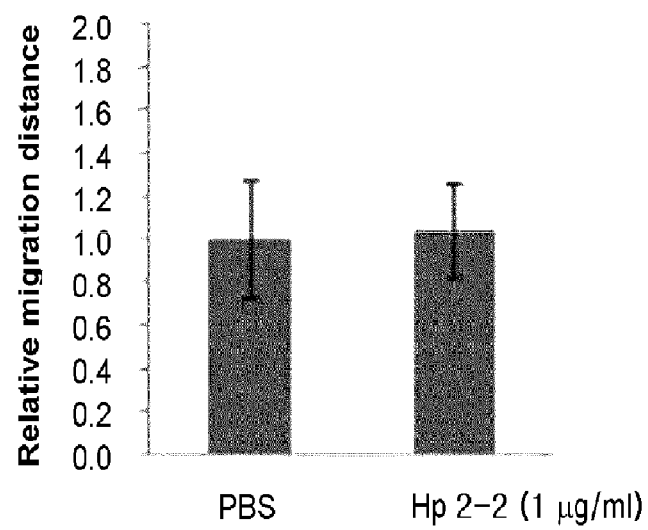
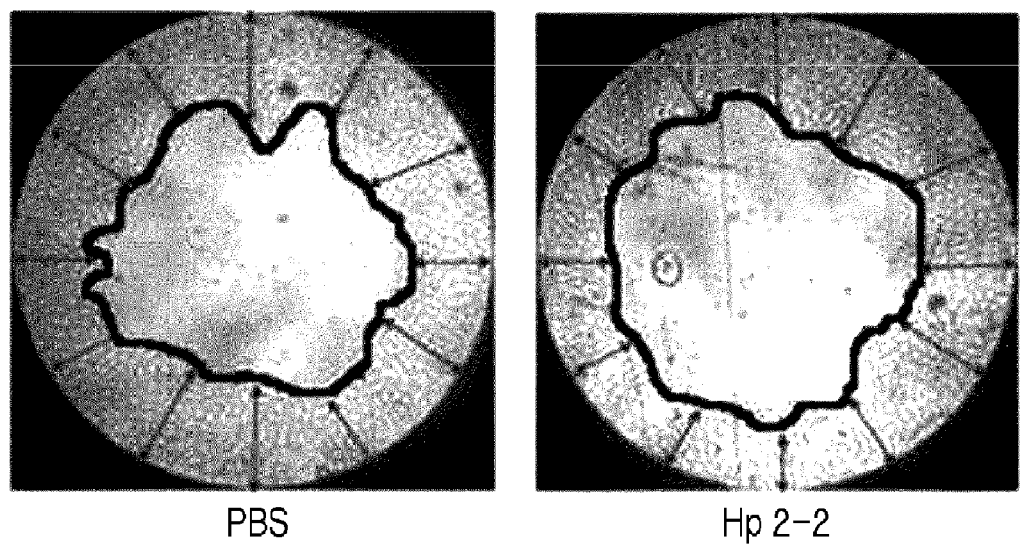

SEQUENCE LISTING

<160> NUMBER OF SEQ ID NOS: 19

<210> SEQ ID NO 1
<211> LENGTH: 388
<212> TYPE: PRT
<213> ORGANISM: Homo sapiens
<220> FEATURE:
<221> NAME/KEY: DOMAIN
<222> LOCATION: (1)..(388)
<223> OTHER INFORMATION: amino acid sequence of prohaptoglobin 2

<400> SEQUENCE: 1

```
Val Asp Ser Gly Asn Asp Val Thr Asp Ile Ala Asp Gly Cys Pro
1               5                   10                  15

Lys Pro Pro Glu Ile Ala His Gly Tyr Val Glu His Ser Val Arg Tyr
                20                  25                  30

Gln Cys Lys Asn Tyr Tyr Lys Leu Arg Thr Glu Gly Asp Gly Val Tyr
            35                  40                  45

Thr Leu Asn Asp Lys Lys Gln Trp Ile Asn Lys Ala Val Gly Asp Lys
        50                  55                  60

Leu Pro Glu Cys Glu Ala Asp Asp Gly Cys Pro Lys Pro Pro Glu Ile
65                  70                  75                  80

Ala His Gly Tyr Val Glu His Ser Val Arg Tyr Gln Cys Lys Asn Tyr
                85                  90                  95

Tyr Lys Leu Arg Thr Glu Gly Asp Gly Val Tyr Thr Leu Asn Asn Glu
            100                 105                 110

Lys Gln Trp Ile Asn Lys Ala Val Gly Asp Lys Leu Pro Glu Cys Glu
        115                 120                 125

Ala Val Cys Gly Lys Pro Lys Asn Pro Ala Asn Pro Val Gln Arg Ile
    130                 135                 140

Leu Gly Gly His Leu Asp Ala Lys Gly Ser Phe Pro Trp Gln Ala Lys
145                 150                 155                 160

Met Val Ser His His Asn Leu Thr Thr Gly Ala Thr Leu Ile Asn Glu
                165                 170                 175

Gln Trp Leu Leu Thr Thr Ala Lys Asn Leu Phe Leu Asn His Ser Glu
            180                 185                 190

Asn Ala Thr Ala Lys Asp Ile Ala Pro Thr Leu Thr Leu Tyr Val Gly
        195                 200                 205

Lys Lys Gln Leu Val Glu Ile Glu Lys Val Val Leu His Pro Asn Tyr
    210                 215                 220

Ser Gln Val Asp Ile Gly Leu Ile Lys Leu Lys Gln Lys Val Ser Val
225                 230                 235                 240

Asn Glu Arg Val Met Pro Ile Cys Leu Pro Ser Lys Asp Tyr Ala Glu
                245                 250                 255

Val Gly Arg Val Gly Tyr Val Ser Gly Trp Gly Arg Asn Ala Asn Phe
            260                 265                 270

Lys Phe Thr Asp His Leu Lys Tyr Val Met Leu Pro Val Ala Asp Gln
        275                 280                 285

Asp Gln Cys Ile Arg His Tyr Glu Gly Ser Thr Val Pro Glu Lys Lys
    290                 295                 300

Thr Pro Lys Ser Pro Val Gly Val Gln Pro Ile Leu Asn Glu His Thr
305                 310                 315                 320

Phe Cys Ala Gly Met Ser Lys Tyr Gln Glu Asp Thr Cys Tyr Gly Asp
                325                 330                 335

Ala Gly Ser Ala Phe Ala Val His Asp Leu Glu Glu Asp Thr Trp Tyr
            340                 345                 350

Ala Thr Gly Ile Leu Ser Phe Asp Lys Ser Cys Ala Val Ala Glu Tyr
        355                 360                 365

Gly Val Tyr Val Lys Val Thr Ser Ile Gln Asp Trp Val Gln Lys Thr
    370                 375                 380

Ile Ala Glu Asn
385
```

<210> SEQ ID NO 2
<211> LENGTH: 388
<212> TYPE: PRT
<213> ORGANISM: Artificial Sequence
<220> FEATURE:
<223> OTHER INFORMATION: R143Q mutated prohaptoglobin 2 sequence of SEQ. ID. NO: 1

<400> SEQUENCE: 2

```
Val Asp Ser Gly Asn Asp Val Thr Asp Ile Ala Asp Asp Gly Cys Pro
1               5                   10                  15

Lys Pro Pro Glu Ile Ala His Gly Tyr Val Glu His Ser Val Arg Tyr
            20                  25                  30

Gln Cys Lys Asn Tyr Tyr Lys Leu Arg Thr Glu Gly Asp Gly Val Tyr
        35                  40                  45

Thr Leu Asn Asp Lys Lys Gln Trp Ile Asn Lys Ala Val Gly Asp Lys
    50                  55                  60

Leu Pro Glu Cys Glu Ala Asp Asp Gly Cys Pro Lys Pro Pro Glu Ile
65                  70                  75                  80

Ala His Gly Tyr Val Glu His Ser Val Arg Tyr Gln Cys Lys Asn Tyr
                85                  90                  95

Tyr Lys Leu Arg Thr Glu Gly Asp Gly Val Tyr Thr Leu Asn Asn Glu
            100                 105                 110

Lys Gln Trp Ile Asn Lys Ala Val Gly Asp Lys Leu Pro Glu Cys Glu
        115                 120                 125

Ala Val Cys Gly Lys Pro Lys Asn Pro Ala Asn Pro Val Gln Gln Ile
    130                 135                 140

Leu Gly Gly His Leu Asp Ala Lys Gly Ser Phe Pro Trp Gln Ala Lys
145                 150                 155                 160

Met Val Ser His His Asn Leu Thr Thr Gly Ala Thr Leu Ile Asn Glu
                165                 170                 175

Gln Trp Leu Leu Thr Thr Ala Lys Asn Leu Phe Leu Asn His Ser Glu
            180                 185                 190

Asn Ala Thr Ala Lys Asp Ile Ala Pro Thr Leu Thr Leu Tyr Val Gly
        195                 200                 205

Lys Lys Gln Leu Val Glu Ile Glu Lys Val Val Leu His Pro Asn Tyr
    210                 215                 220

Ser Gln Val Asp Ile Gly Leu Ile Lys Leu Lys Gln Lys Val Ser Val
225                 230                 235                 240

Asn Glu Arg Val Met Pro Ile Cys Leu Pro Ser Lys Asp Tyr Ala Glu
                245                 250                 255

Val Gly Arg Val Gly Tyr Val Ser Gly Trp Gly Arg Asn Ala Asn Phe
            260                 265                 270

Lys Phe Thr Asp His Leu Lys Tyr Val Met Leu Pro Val Ala Asp Gln
        275                 280                 285

Asp Gln Cys Ile Arg His Tyr Glu Gly Ser Thr Val Pro Glu Lys Lys
    290                 295                 300

Thr Pro Lys Ser Pro Val Gly Val Gln Pro Ile Leu Asn Glu His Thr
305                 310                 315                 320

Phe Cys Ala Gly Met Ser Lys Tyr Gln Glu Asp Thr Cys Tyr Gly Asp
                325                 330                 335

Ala Gly Ser Ala Phe Ala Val His Asp Leu Glu Glu Asp Thr Trp Tyr
            340                 345                 350

Ala Thr Gly Ile Leu Ser Phe Asp Lys Ser Cys Ala Val Ala Glu Tyr
```

```
                    355                 360                 365
Gly Val Tyr Val Lys Val Thr Ser Ile Gln Asp Trp Val Gln Lys Thr
            370                 375                 380

Ile Ala Glu Asn
385

<210> SEQ ID NO 3
<211> LENGTH: 388
<212> TYPE: PRT
<213> ORGANISM: Artificial Sequence
<220> FEATURE:
<223> OTHER INFORMATION: R143L mutated prohaptoglobin 2 sequence of SEQ.
      ID. NO: 1

<400> SEQUENCE: 3

Val Asp Ser Gly Asn Asp Val Thr Asp Ile Ala Asp Asp Gly Cys Pro
1               5                   10                  15

Lys Pro Pro Glu Ile Ala His Gly Tyr Val Glu His Ser Val Arg Tyr
            20                  25                  30

Gln Cys Lys Asn Tyr Tyr Lys Leu Arg Thr Glu Gly Asp Gly Val Tyr
        35                  40                  45

Thr Leu Asn Asp Lys Lys Gln Trp Ile Asn Lys Ala Val Gly Asp Lys
    50                  55                  60

Leu Pro Glu Cys Glu Ala Asp Asp Gly Cys Pro Lys Pro Pro Glu Ile
65                  70                  75                  80

Ala His Gly Tyr Val Glu His Ser Val Arg Tyr Gln Cys Lys Asn Tyr
                85                  90                  95

Tyr Lys Leu Arg Thr Glu Gly Asp Gly Val Tyr Thr Leu Asn Asn Glu
            100                 105                 110

Lys Gln Trp Ile Asn Lys Ala Val Gly Asp Lys Leu Pro Glu Cys Glu
        115                 120                 125

Ala Val Cys Gly Lys Pro Lys Asn Pro Ala Asn Pro Val Gln Leu Ile
    130                 135                 140

Leu Gly Gly His Leu Asp Ala Lys Gly Ser Phe Pro Trp Gln Ala Lys
145                 150                 155                 160

Met Val Ser His His Asn Leu Thr Thr Gly Ala Thr Leu Ile Asn Glu
                165                 170                 175

Gln Trp Leu Leu Thr Thr Ala Lys Asn Leu Phe Leu Asn His Ser Glu
            180                 185                 190

Asn Ala Thr Ala Lys Asp Ile Ala Pro Thr Leu Thr Leu Tyr Val Gly
        195                 200                 205

Lys Lys Gln Leu Val Glu Ile Glu Lys Val Val Leu His Pro Asn Tyr
    210                 215                 220

Ser Gln Val Asp Ile Gly Leu Ile Lys Leu Lys Gln Lys Val Ser Val
225                 230                 235                 240

Asn Glu Arg Val Met Pro Ile Cys Leu Pro Ser Lys Asp Tyr Ala Glu
                245                 250                 255

Val Gly Arg Val Gly Tyr Val Ser Gly Trp Gly Arg Asn Ala Asn Phe
            260                 265                 270

Lys Phe Thr Asp His Leu Lys Tyr Val Met Leu Pro Val Ala Asp Gln
        275                 280                 285

Asp Gln Cys Ile Arg His Tyr Glu Gly Ser Thr Val Pro Glu Lys Lys
    290                 295                 300

Thr Pro Lys Ser Pro Val Gly Val Gln Pro Ile Leu Asn Glu His Thr
305                 310                 315                 320
```

-continued

```
Phe Cys Ala Gly Met Ser Lys Tyr Gln Glu Asp Thr Cys Tyr Gly Asp
                325                 330                 335
Ala Gly Ser Ala Phe Ala Val His Asp Leu Glu Glu Asp Thr Trp Tyr
            340                 345                 350
Ala Thr Gly Ile Leu Ser Phe Asp Lys Ser Cys Ala Val Ala Glu Tyr
        355                 360                 365
Gly Val Tyr Val Lys Val Thr Ser Ile Gln Asp Trp Val Gln Lys Thr
    370                 375                 380
Ile Ala Glu Asn
385
```

<210> SEQ ID NO 4
<211> LENGTH: 1164
<212> TYPE: DNA
<213> ORGANISM: Artificial Sequence
<220> FEATURE:
<223> OTHER INFORMATION: nucleotide sequence for amino acid sequence of
      SEQ. ID. NO: 2

<400> SEQUENCE: 4

```
gtggactcag gcaatgatgt cacggatatc gcagatgacg gctgcccgaa gcccccgag      60
attgcacatg gctatgtgga gcactcggtt cgctaccagt gtaagaacta ctacaaactg    120
cgcacagaag gagatggagt atacaccta aatgataaga agcagtggat aaataaggct     180
gttggagata aacttcctga atgtgaagca gatgacggct gcccgaagcc ccccgagatt    240
gcacatggct atgtggagca ctcggttcgc taccagtgta agaactacta caaactgcgc    300
acagaaggag atggagtgta cacccttaaac aatgagaagc agtggataaa taaggctgtt   360
ggagataaac ttcctgaatg tgaagcagta tgtgggaagc caagaatcc ggcaaaccca     420
gtgcagcaga tcctgggtgg acacctggat gccaaaggca gctttccctg caggctaag    480
atggtttccc accataatct caccacaggt gccacgctga tcaatgaaca atggctgctg   540
accacggcta aaaatctctt cctgaaccat tcagaaaatg caacagcgaa agacattgcc   600
cctactttaa cactctatgt ggggaaaaag cagcttgtag agattgagaa ggttgttcta   660
caccctaact actcccaggt agatattggg ctcatcaaac tcaaacagaa ggtgtctgtt   720
aatgagagag tgatgcccat ctgcctacct tcaaaggatt atgcagaagt agggcgtgtg   780
ggttatgttt ctggctgggg cgaaatgcc aatttttaaat ttactgacca tctgaagtat   840
gtcatgctgc ctgtggctga ccaagaccaa tgcataaggc attatgaagg cagcacagtc   900
cccgaaaaga agacaccgaa gagccctgta ggggtgcagc ccatactgaa tgaacacacc   960
ttctgtgctg gcatgtctaa gtaccaagaa gacacctgct atggcgatgc gggcagtgcc  1020
tttgccgttc acgacctgga ggaggacacc tggtatgcga ctgggatctt aagctttgat  1080
aagagctgtg ctgtggctga gtatggtgtg tatgtgaagg tgacttccat ccaggactgg  1140
gttcagaaga ccatagctga gaac                                          1164
```

<210> SEQ ID NO 5
<211> LENGTH: 1164
<212> TYPE: DNA
<213> ORGANISM: Artificial Sequence
<220> FEATURE:
<223> OTHER INFORMATION: nucleotide sequence for amino acid sequence of
      SEQ. ID. NO: 3

<400> SEQUENCE: 5

```
gtggactcag gcaatgatgt cacggatatc gcagatgacg gctgcccgaa gcccccgag      60
```

```
attgcacatg gctatgtgga gcactcggtt cgctaccagt gtaagaacta ctacaaactg    120
cgcacagaag gagatggagt atacaccta aatgataaga agcagtggat aaataaggct    180
gttggagata aacttcctga atgtgaagca gatgacggct gcccgaagcc ccccgagatt    240
gcacatggct atgtggagca ctcggttcgc taccagtgta agaactacta caaactgcgc    300
acagaaggag atggagtgta caccttaaac aatgagaagc agtggataaa taaggctgtt    360
ggagataaac ttcctgaatg tgaagcagta tgtgggaagc caagaatcc ggcaaaccca    420 gtgcagctga tcctgggtgg cacctggat gccaaaggca gctttccctg caggctaag    480 atggtttccc accataatct caccacaggt gccacgctga tcaatgaaca atggctgctg    540
accacggcta aaaatctctt cctgaaccat tcagaaaatg caacagcgaa agacattgcc    600
cctactttaa cactctatgt ggggaaaaag cagcttgtag agattgagaa ggttgttcta    660
caccctaact actcccaggt agatattggg ctcatcaaac tcaaacagaa ggtgtctgtt    720
aatgagagag tgatgcccat ctgcctacct tcaaaggatt atgcagaagt agggcgtgtg    780
ggttatgttt ctggctgggg cgaaatgcc aattttaaat ttactgacca tctgaagtat    840
gtcatgctgc ctgtggctga ccaagaccaa tgcataaggc attatgaagg cagcacagtc    900
cccgaaaaga agacaccgaa gagccctgta ggggtgcagc ccatactgaa tgaacacacc    960
ttctgtgctg gcatgtctaa gtaccaagaa gacacctgct atggcgatgc gggcagtgcc   1020
tttgccgttc acgacctgga ggaggacacc tggtatgcga ctgggatctt aagctttgat   1080
aagagctgtg ctgtggctga gtatggtgtg tatgtgaagg tgacttccat ccaggactgg   1140
gttcagaaga ccatagctga gaac                                          1164
```

<210> SEQ ID NO 6
<211> LENGTH: 142
<212> TYPE: PRT
<213> ORGANISM: Homo sapiens
<220> FEATURE:
<221> NAME/KEY: DOMAIN
<222> LOCATION: (1)..(142)
<223> OTHER INFORMATION: alpha chain amino acid sequence of haptoglobin 2

<400> SEQUENCE: 6

```
Val Asp Ser Gly Asn Asp Val Thr Asp Ile Ala Asp Asp Gly Cys Pro
1               5                   10                  15

Lys Pro Pro Glu Ile Ala His Gly Tyr Val Glu His Ser Val Arg Tyr
            20                  25                  30

Gln Cys Lys Asn Tyr Tyr Lys Leu Arg Thr Glu Gly Asp Gly Val Tyr
        35                  40                  45

Thr Leu Asn Asp Lys Lys Gln Trp Ile Asn Lys Ala Val Gly Asp Lys
    50                  55                  60

Leu Pro Glu Cys Glu Ala Asp Asp Gly Cys Pro Lys Pro Pro Glu Ile
65                  70                  75                  80

Ala His Gly Tyr Val Glu His Ser Val Arg Tyr Gln Cys Lys Asn Tyr
                85                  90                  95

Tyr Lys Leu Arg Thr Glu Gly Asp Gly Val Tyr Thr Leu Asn Asn Glu
            100                 105                 110

Lys Gln Trp Ile Asn Lys Ala Val Gly Asp Lys Leu Pro Glu Cys Glu
        115                 120                 125

Ala Val Cys Gly Lys Pro Lys Asn Pro Ala Asn Pro Val Gln
    130                 135                 140
```

```
<210> SEQ ID NO 7
<211> LENGTH: 245
<212> TYPE: PRT
<213> ORGANISM: Homo sapiens
<220> FEATURE:
<221> NAME/KEY: DOMAIN
<222> LOCATION: (1)..(245)
<223> OTHER INFORMATION: beta chain amino acid sequence of haptoglobin 2

<400> SEQUENCE: 7

Ile Leu Gly Gly His Leu Asp Ala Lys Gly Ser Phe Pro Trp Gln Ala
1               5                   10                  15

Lys Met Val Ser His His Asn Leu Thr Thr Gly Ala Thr Leu Ile Asn
            20                  25                  30

Glu Gln Trp Leu Leu Thr Thr Ala Lys Asn Leu Phe Leu Asn His Ser
        35                  40                  45

Glu Asn Ala Thr Ala Lys Asp Ile Ala Pro Thr Leu Thr Leu Tyr Val
    50                  55                  60

Gly Lys Lys Gln Leu Val Glu Ile Glu Lys Val Val Leu His Pro Asn
65                  70                  75                  80

Tyr Ser Gln Val Asp Ile Gly Leu Ile Lys Leu Lys Gln Lys Val Ser
                85                  90                  95

Val Asn Glu Arg Val Met Pro Ile Cys Leu Pro Ser Lys Asp Tyr Ala
            100                 105                 110

Glu Val Gly Arg Val Gly Tyr Val Ser Gly Trp Gly Arg Asn Ala Asn
        115                 120                 125

Phe Lys Phe Thr Asp His Leu Lys Tyr Val Met Leu Pro Val Ala Asp
    130                 135                 140

Gln Asp Gln Cys Ile Arg His Tyr Glu Gly Ser Thr Val Pro Glu Lys
145                 150                 155                 160

Lys Thr Pro Lys Ser Pro Val Gly Val Gln Pro Ile Leu Asn Glu His
                165                 170                 175

Thr Phe Cys Ala Gly Met Ser Lys Tyr Gln Glu Asp Thr Cys Tyr Gly
            180                 185                 190

Asp Ala Gly Ser Ala Phe Ala Val His Asp Leu Glu Glu Asp Thr Trp
        195                 200                 205

Tyr Ala Thr Gly Ile Leu Ser Phe Asp Lys Ser Cys Ala Val Ala Glu
    210                 215                 220

Tyr Gly Val Tyr Val Lys Val Thr Ser Ile Gln Asp Trp Val Gln Lys
225                 230                 235                 240

Thr Ile Ala Glu Asn
            245

<210> SEQ ID NO 8
<211> LENGTH: 33
<212> TYPE: DNA
<213> ORGANISM: Artificial Sequence
<220> FEATURE:
<223> OTHER INFORMATION: Hp2-F primer

<400> SEQUENCE: 8
gcgaattcgc caccatgagt gccctgggag ctg                                   33

<210> SEQ ID NO 9
<211> LENGTH: 32
<212> TYPE: DNA
<213> ORGANISM: Artificial Sequence
<220> FEATURE:
<223> OTHER INFORMATION: Hp2-R primer
```

```
<400> SEQUENCE: 9
ccggtaccgt tctcagctat ggtcttctga ac                                32

<210> SEQ ID NO 10
<211> LENGTH: 33
<212> TYPE: DNA
<213> ORGANISM: Artificial Sequence
<220> FEATURE:
<223> OTHER INFORMATION: Hp2-R143Q-F primer

<400> SEQUENCE: 10
gcaaacccag tgcagcagat cctgggtgga cac                               33

<210> SEQ ID NO 11
<211> LENGTH: 33
<212> TYPE: DNA
<213> ORGANISM: Artificial Sequence
<220> FEATURE:
<223> OTHER INFORMATION: Hp2-R143Q-R primer

<400> SEQUENCE: 11
gtgtccaccc aggatctgct gcactgggtt tgc                               33

<210> SEQ ID NO 12
<211> LENGTH: 33
<212> TYPE: DNA
<213> ORGANISM: Artificial Sequence
<220> FEATURE:
<223> OTHER INFORMATION: Hp2-R143L-F primer

<400> SEQUENCE: 12
gcaaacccag tgcagctgat cctgggtgga cac                               33

<210> SEQ ID NO 13
<211> LENGTH: 33
<212> TYPE: DNA
<213> ORGANISM: Artificial Sequence
<220> FEATURE:
<223> OTHER INFORMATION: Hp2-R143L-R primer

<400> SEQUENCE: 13
gtgtccaccc aggatcagct gcactgggtt tgc                               33

<210> SEQ ID NO 14
<211> LENGTH: 21
<212> TYPE: DNA
<213> ORGANISM: Artificial Sequence
<220> FEATURE:
<223> OTHER INFORMATION: VEGF-F primer

<400> SEQUENCE: 14
gcggagaaag catttgtttg t                                            21

<210> SEQ ID NO 15
<211> LENGTH: 19
<212> TYPE: DNA
<213> ORGANISM: Artificial Sequence
<220> FEATURE:
<223> OTHER INFORMATION: VEGF-R primer

<400> SEQUENCE: 15
ttgcagatgt gacaagccg                                               19

<210> SEQ ID NO 16
<211> LENGTH: 22
```

```
<212> TYPE: DNA
<213> ORGANISM: Artificial Sequence
<220> FEATURE:
<223> OTHER INFORMATION: VEGFR2-F primer

<400> SEQUENCE: 16
tgggaaccgg aacctcacta tc                                              22

<210> SEQ ID NO 17
<211> LENGTH: 24
<212> TYPE: DNA
<213> ORGANISM: Artificial Sequence
<220> FEATURE:
<223> OTHER INFORMATION: VEGFR2-R primer

<400> SEQUENCE: 17
gtcttttcct gggcaccttc tatt                                            24

<210> SEQ ID NO 18
<211> LENGTH: 20
<212> TYPE: DNA
<213> ORGANISM: Artificial Sequence
<220> FEATURE:
<223> OTHER INFORMATION: GAPDH-F primer

<400> SEQUENCE: 18
accacagtcc atgccatcac                                                 20

<210> SEQ ID NO 19
<211> LENGTH: 20
<212> TYPE: DNA
<213> ORGANISM: Artificial Sequence
<220> FEATURE:
<223> OTHER INFORMATION: GAPDH-R primer

<400> SEQUENCE: 19
tccaccaccc tgttgctgta                                                 20
```

USE OF MUTANT HAPTOGLOBIN HAVING ANGIOGENESIS PROMOTING ACTIVITY

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "2015-07-14 1883-5 PCT US ST25.txt" created on Jul. 14, 2015 and is 19,970 bytes in size. The sequence listing contained in this .txt file is part of the specification and is hereby incorporated by reference herein in its entirety.

TECHNICAL FIELD

The present invention relates to a use of the mutant haptoglobin having the activity of promoting angiogenesis. More precisely, the present invention relates to a recombinant vector introduced with the mutant haptoglobin polynucleotide or a composition for promoting angiogenesis comprising the mutant haptoglobin polypeptide as an active ingredient.

BACKGROUND ART

Ischemic tissue damage needs angiogenesis in the damaged area for the tissue recovery. After birth, new vessels are generated by angiogenesis, arteriogenesis, and vasculogenesis. Angiogenesis is related to the proliferation and migration of endothelial cells that are developed from the mature endothelial cells, while arteriogenesis is the process of remodeling of arteriolar connection as collateral vessels (Carmeliet, P. (2000) Mechanisms of angiogenesis and arteriogenesis. Nat. Med. 6, 389.395). In the meantime, vasculogenesis is progressed through the course wherein endothelial progenitor cells (EPC) are developed into the mature endothelial cells (Asahara, T. and Kawamoto, A. (2004) Endothelial progenitor cells for postnatal vasculogenesis. Am. J. Physiol. Cell Physiol. 287, 572.579.). EPCs that are developed from the bone marrow and circulated thereafter to migrate to the area of injury of blood vessels and are involved in angiogenesis by being inserted directly in the newly generated blood vessels or by inducing the secretion of various angiogenesis factors and nutritional factors (Jujo, K., Ii, M. and Losordo, D. W. (2008) Endothelial progenitor cells in neovascularization of infracted myocardium. J. Mol. Cell. Cardiol. 45, 530.544., Urbich, C., Aicher, A., Heeschen, C., Dernbach, E., Hofmann, W. K., Zeiher, A. M. and Dimmeler, S. (2005) Soluble factors released by endothelial progenitor cells promote migration of endothelial cells and cardiac resident progenitor cells. J. Mol. Cell. Cardiol. 39, 733.742.). Therefore, EPCs are the potential target of concern for the treatment by revascularization (Jujo, K., Ii, M. and Losordo, D. W. (2008) Endothelial progenitor cells in neovascularization of infracted myocardium. J. Mol. Cell. Cardiol. 45, 530.544.).

Recent studies on EPCs are mainly focused on the EPCs that are genetically modified ex vivo in order to increase the functions of cells. For that purpose, vascular endothelial growth factor (VEGF) and hypoxia-inducible factor-1a have been used because they displayed the activity of increasing the pro-angiogenic capacity of EPCs (Iwaguro, H., Yamaguchi, J., Kalka, C., Murasawa, S., Masuda, H., Hayashi, S., Silver, M., Li, T., Isner, J. M. and Asahara, T. (2002) Endothelial progenitor cell vascular endothelial growth factor gene transfer for vascular regeneration. Circulation 105, 732.738., Jiang, M., Wang, B., Wang, C., He, B., Fan, H., Guo, T. B., Shao, Q., Gao, L. and Liu, Y. (2008) Angiogenesis by transplantation of HIF-1a modified EPCs into ischemic limbs. J. Cell. Biochem. 103, 321.334.).

Haptoglobin (Hp) is an acute-phase glycoprotein existing in blood circulation system, and the well known biological function of Hp is capturing hemoglobin. Hp forms HP-hemoglobin complex which is known to be functioning to prevent hemoglobin-stimulated oxidative tissue damage (Lim, Y. K., Jenner, A., Ali, A. B., Wang, Y., Hsu, S. I., Chong, S. M., Baumman, H., Halliwell, B. and Lim, S. K. (2000) Haptoglobin reduces renal oxidative DNA and tissue damage during phenylhydrazine-induced hemolysis. Kidney Int. 58, 1033.1044., Buehler, P. W., Abraham, B., Vallelian, F., Linnemayr, C., Pereira, C. P., Cipollo, J. F., Jia, Y., Mikolajczyk, M., Boretti, F. S., Schoedon, G., Alayash, A. I. and Schaer, D. J. (2009) Haptoglobin preserves the CD163 hemoglobin scavenger pathway by shielding hemoglobin from peroxidative modification. Blood 113, 2578.2586).

Hp can be expressed in artery (Smeets, M. B., Pasterkamp, G., Lim, S. K., Velema, E., van Middelaar, B. and de Kleijn, D. P. V. (2002) Nitric oxide synthesis is involved in arterial haptoglobin expression after sustained flow changes. FEBS Lett. 529, 221.224.) and thus can be functioning as a cell migration factor that is particularly involved in arterial restructuring (de Kleijn, D. P. V., Smeets, M. B., Kemmeren, P. P. C. W., Lim, S. K., van Middelaar, B. J., Velema, E., Schoneveld, A., Pasterkamp, G. and Borst, C. (2002) Acutephase protein haptoglobin is a cell migration factor involved in arterial restructuring. FASEB J. 16, 1123.1125., Lohr, N. L., Warltier, D. C., Chilian, W. M. and Weihrauch, D. (2005) Haptoglobin expression and activity during coronary collateralization. Am. J. Physiol. Heart Circ. Physiol. 288, H1389.H1395).

However, there are no reports so far that suggest the mutant haptoglobin can induce angiogenesis.

Therefore, the present inventors studied and confirmed that the mutant haptoglobin had the higher activity of promoting angiogenesis than that of the wild type haptoglobin, leading to the completion of this invention.

SUMMARY

Technical Problem

It is an object of the present invention to provide a mutant haptoglobin polypeptide composed of the amino acid sequence wherein the $143^{rd}$ amino acid of the sequence represented by SEQ. ID. NO: 1 is substituted with another amino acid other than Arg.

It is another object of the present invention to provide a polynucleotide encoding the said polypeptide above.

It is further an object of the present invention to provide a recombinant vector comprising the said polynucleotide.

It is also an object of the present invention to provide a transformant transfected with the said recombinant vector.

It is also an object of the present invention to provide a composition for promoting angiogenesis comprising the mutant haptoglobin polypeptide or the recombinant vector harboring the polynucleotide encoding the polypeptide.

Technical Solution

To achieve the above objects, the present invention provides a mutant haptoglobin polypeptide composed of the amino acid sequence wherein the $143^{rd}$ amino acid of the sequence represented by SEQ. ID. NO: 1 is substituted with another amino acid other than Arg.

In a preferred embodiment of the present invention, the mutant haptoglobin is characterized by the inhibition of the site-specific cleavage of the 143$^{rd}$ amino acid of the sequence represented by SEQ. ID. NO: 1.

In a preferred embodiment of the present invention, the mutant haptoglobin is characterized by having the amino acid sequence represented by SEQ. ID. NO: 2 wherein Arg, the 143$^{rd}$ amino acid of the sequence represented by SEQ. ID. NO: 1, has been substituted with Gln.

In a preferred embodiment of the present invention, the mutant haptoglobin is characterized by having the amino acid sequence represented by SEQ. ID. NO: 3 wherein Arg, the 143$^{rd}$ amino acid of the sequence represented by SEQ. ID. NO: 1, has been substituted with Leu.

The present invention also provides a polynucleotide encoding the mutant haptoglobin polypeptide.

In a preferred embodiment of the present invention, the said polynucleotide is characteristically composed of the nucleotide sequence represented by SEQ. ID. NO: 4 encoding the mutant haptoglobin polypeptide having the amino acid sequence represented by SEQ. ID. NO: 2.

In a preferred embodiment of the present invention, the said polynucleotide is characteristically composed of the nucleotide sequence represented by SEQ. ID. NO: 5 encoding the mutant haptoglobin polypeptide having the amino acid sequence represented by SEQ. ID. NO: 3.

The present invention also provides a recombinant vector comprising the said polynucleotide.

The present invention also provides a transformant transfected with the said recombinant vector.

In addition, the present invention provides a composition for promoting angiogenesis comprising the mutant haptoglobin polypeptide or the recombinant vector harboring the polynucleotide encoding the polypeptide.

In a preferred embodiment of the present invention, the composition can be efficiently used for the prevention or treatment of disease selected from the group consisting of angiogenesis-defect related diseases such as diabetic ulcer, gangrene, ischemic diseases, occlusive vascular diseases, cardiovascular diseases, and local ischemia.

BRIEF DESCRIPTION OF DRAWINGS

FIG. 1 is a schematic diagram illustrating the amino acid sequences of α chain (SEQ. ID. NO: 6) and β chain (SEQ. ID. NO: 7) of the wild-type haptoglobin protein (Hp 2-2).

FIG. 2 is a schematic diagram illustrating the amino acid sequence of the mutant haptoglobin represented by SEQ. ID. NO: 2, wherein the 143$^{rd}$ amino acid Arg of the wild-type prohaptoglobin (prohaptoglobin2) is substituted with Gln.

FIG. 3 is a schematic diagram illustrating the amino acid sequence of the mutant haptoglobin represented by SEQ. ID. NO: 3, wherein the 143$^{rd}$ amino acid Arg of the wild-type prohaptoglobin (prohaptoglobin2) is substituted with Leu.

FIG. 4a~FIG. 4c present the results of Western blotting showing the cleavage of the wild-type haptoglobin (Hp2-2) and the mutant haptoglobin (mutant Hp).

FIG. 5a and FIG. 5b present the results of qRT-PCR measuring the levels of mRNA of VEGF and VEGFR2 of HUVEC cells treated with the wild-type haptoglobin or the mutant haptoglobin.

FIG. 6 presents the result of observation of capillary-like tube formation in HUVEC cells treated with the wild-type haptoglobin or the mutant haptoglobin.

FIG. 7a~FIG. 7c present the results of measuring the distance of cell migration in HUVEC cells treated with the wild-type haptoglobin or the mutant haptoglobin.

DETAILED DESCRIPTION

Figure 4A:
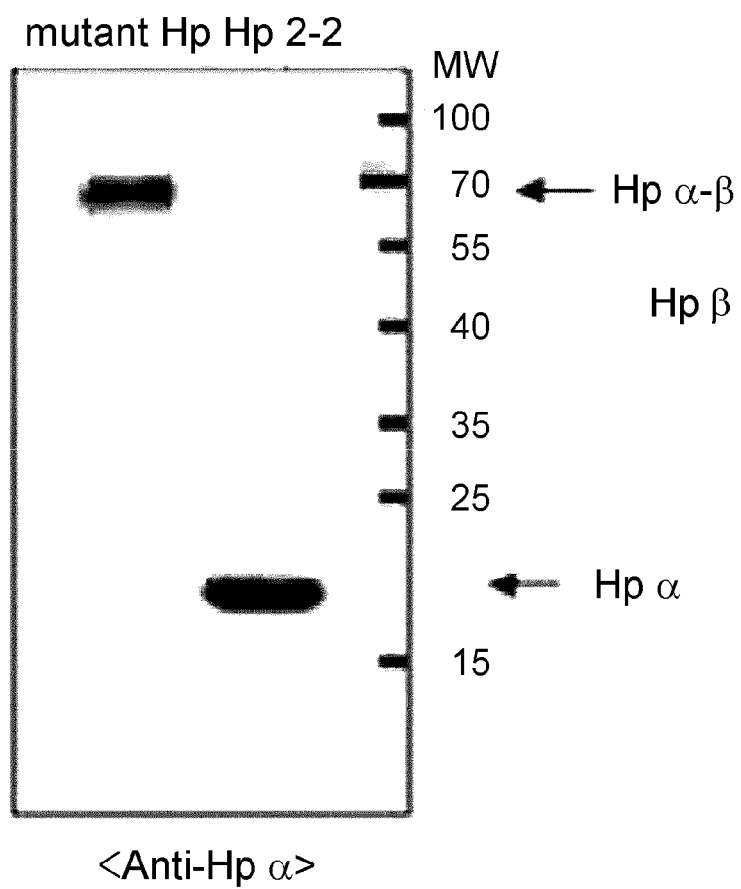

Hereinafter, the present invention is described in detail.

The present invention provides a recombinant vector comprising the mutant haptoglobin polynucleotide and a mutant haptoglobin polypeptide.

Angiogenesis is a highly sophisticated process to generate new blood vessels mediated by not only growth factors, cytokines, and other physiological factors but also various angiogenic factors including hypoxia and low pH, etc. (Folkman and Shing, *J. Biol. Chem.*, 267, 10931, 1992). To develop new blood vessels, angiogenesis mechanism needs cooperation with various molecules that regulate or are involved in degradation/reconstruction, migration, proliferation, differentiation, and tube-formation of extra-cellular matrix (ECM). Once new blood vessels begin to be formed, angiogenic factors including VEGF, bFGF, and PDGF activate endothelial cells by stimulating the receptor on the cell surface and then the activated cells induce the proliferation of cells, the expression of cell adhesion molecules, the secretion of proteolytic enzymes, and the migration/infiltration of cells. Various molecules including integrin for cell adhesion, selectin, immunoglobulin gene superfamily components, matrix metaloprotease for ECM degradation, and serine protease induce the proliferation and infiltration of cells (Brooks, Eur. *J. Cancer,* 32A, 2423, 1996). Further, Lumen formation and differentiation to mature blood vessels are induced by signal transduction mechanism mediated by the cell surface receptor that can interact with ECM and lytic factors, resulting in angiogenesis.

Recently, the attempts have been made to treat angiogenesis mediated diseases such as cancer, rheumatoid arthritis, psoriasis, ulcer, ischemia, atherosclerosis, myocardial infarction, angina pectoris, and cerebrovascular disease by using angiogenesis promoters or angiogenesis inhibitors (Folkman J., *J. Nat. Med.*, 1:27, 1995; Jackson J. R., et al., *FASEB J.*, 11:457, 1997; Risau W., *Nature,* 386:671, 1997; Bussolino, F., et al., Trends Biochem. Sci., 22:251, 1997; Hanahan D., et al., *Cell,* 86:353, 1996).

The replacement of endothelial cells composing blood vessels, in normal adults, takes 47~20,000 days, which is strictly regulated. In general, the angiogenesis inhibitors such as thrombospondin-1, platelet factor-4, and angiostatin and the angiogenesis promoters such as vascular endothelial growth factor (VEGF) and basic fibroblast growth factor (bFGF) are quantitatively balanced, so as not to induce angiogenesis. However, when a wound or cancer is developed, the balance between the angiogenesis inhibitors and the angiogenesis promoters is broken in order to induce the regeneration of wound tissue and the growth of cancer which require new blood vessel formation. At this time, the angiogenesis promoters are over-expressed.

The excessive new blood vessel formation can be a major cause of aggravation of disease and at the same time the blood vessel non-formation can also be a cause of severe disease. Angiogenesis is an essential phenomenon for wound healing or tissue regeneration. For example, undeveloped angiogenesis in placenta results in miscarriage. Undeveloped angiogenesis also causes necrosis, ulcer, and ischemia, which further results in the malfunction of tissues or organs or even death. Atherosclerosis, myocardial infarction, and angina pectoris are also caused by irregular blood circulation.

Therefore, it is very important to induce or promote angiogenesis in order to reduce tissue damage caused by hypoxia or mal-nutrition resulted from non-formation of blood vessels and to induce tissue regeneration thereafter. In particular, angiogenesis is an essential process for the regeneration of skin tissue on the wounded region. In the early stage of wound, inflammatory response is accompanied because of cell necrosis and blood vessel destruction. After the inflammatory response, a series of reactions such as escape of blood components, platelet activation, blood coagulation, and the production of biological mediators such as kallikrein, thrombin, and plasmin follow.

The treatment of biological disease using angiogenesis is called 'angiogenesis therapy'. Angiogenesis promoting factors, such as vascular endothelial growth factor (VEGF), have already been used as a therapeutic agent for severe local ischemia. Other angiogenesis promoting factors such as fibroblast growth factor, epidermal growth factor, and platelet-derived endothelial growth factor are now the targets of study for clinical use.

In this invention, the mutant haptoglobin is used for the treatment of disease caused by the non-formation of blood vessels. In particular, the present inventors firstly confirmed that the haptoglobin represented by SEQ. ID. NO: 1 wherein the $143^{rd}$ amino acid Arg has been mutated so that site specific cleavage is not induced thereon to preserve precursor form has excellent angiogenesis promoting activity.

Human displays allelic polymorphism against haptoglobin (Hp). According to the two major alleles, $Hp^1$ and $Hp^2$, haptoglobin is expressed as three major characters, which are Hp 1-1 ($Hp^1/Hp^1$), Hp 2-1 ($Hp^1/Hp^2$) and Hp 2-2 ($Hp^2/Hp^2$) (Maeda, N., Yang, F., Barnett, D. R., Bowman, B. H. and Smithies, O. (1984) Duplication within the haptoglobin Hp2 gene. *Nature* 309, 131.135.). Hp 2-2 is known to have stronger angiogenesis promoting activity than Hp 1-1 (Cid, et al. (1993) Identification of haptoglobin as an angiogenic factor in sera from patients with systemic vasculitis. *J. Clin. Invest.* 91, 977.985.).

Regarding Hp2-2, Hp2 gene is expressed in cells and then synthesized as one preprohaptoglobin wherein α chain and β chain are linked together. The signal sequence composed of 18 amino acids at N-terminal is eliminated, resulting in the prohaptoglobin composed of 388 amino acids. Then, site specific cleavage occurs at Arg, the $143^{rd}$ residue, to eliminate the $143^{rd}$ amino acids Arg, so that the sequence is divided into two parts which are α chain composed of 142 amino acids and β chain composed of 245 amino acids. These α chain and β chain are linked by disulfide bond, leading to the production of a polymer. The produced polymer is then secreted extracellularly.

In the meantime, the factors presumed to be involved in angiogenesis were isolated from the serum of a systemic vasculitis patient, followed by investigation. As a result, it was confirmed that the level of haptoglobin therein was higher than in a normal person. In vitro tube formation on Matrigel was investigated using the isolated haptoglobin 2-2 (Hp 2-2). As a result, the formation was confirmed at the concentration of 20 μg/ml or higher.

The present inventors also confirmed that the angiogenesis promoting effect was greater by prohaptoglobin, the precursor form of haptoglobin, than by haptoglobin 2-2 (Hp 2-2), the mature form of haptoglobin.

The present invention also provides a polynucleotide encoding the mutant haptoglobin wherein the $143^{rd}$ amino acid 'Arg' of the sequence represented by SEQ. ID. NO: 1 is substituted with Gln or Leu so as to inhibit the synthesis of mature haptoglobin 2-2 (Hp 2-2). At this time, the polynucleotide can contain all of DNA, cDNA, and RNA sequences.

The present invention also provides a recombinant vector containing the polynucleotide encoding the mutant haptoglobin. In this invention, the recombinant vector containing the polynucleotide encoding the mutant haptoglobin is an expression vector wherein the gene of the mutant haptoglobin is operably linked to the promoter of the vector. The expression vector usable in this invention can be any plasmid, virus, or other mediators that are well known to those in the art, but not always limited thereto. Particularly, lentivirus vector is preferred in this invention.

The recombinant vector of the present invention can be introduced in cells by the conventional method well known to those in the art. For example, the vector can be inserted in cells by transient transfection, microinjection, transduction, cell fusion, calcium phosphate precipitation, liposome-mediated transfection, DEAE dextran-mediated transfection, polybrene-mediated transfection, electroporation, gene gun, and any conventional method to insert nucleic acid in cells (Wu et al., J. Bio. Chem., 267:963-967, 1992; Wu and Wu, J. Bio. Chem., 263:14621-14624, 1988), but not always limited thereto.

In a preferred embodiment of the present invention, in order to replace the $143^{rd}$ amino acid Arg of the wild-type haptoglobin (Hp2) represented by SEQ. ID. NO: 1 with Gln or Leu, the mutant haptoglobin gene having the nucleotide sequence represented by SEQ. ID. NO: 4 or SEQ. ID. NO: 5 was constructed, which was then inserted in pcDNA3.0 vector, resulting in the construction of the recombinant vector. The constructed recombinant vector was inserted in cells via transfection. The transformant introduced with the mutant haptoglobin of the invention displayed the accelerated blood vessel differentiation by the mutant haptoglobin expressed therein, indicating that the mutant haptoglobin had the activity of promoting angiogenesis.

The present invention also provides a mutant haptoglobin polypeptide composed of the amino acid sequence wherein the $143^{rd}$ amino acid of the wild-type haptoglobin amino acid sequence is substituted with another amino acid other than Arg.

The said polypeptide can include the mutant haptoglobin protein which lost site specific cleavage capacity because of the mutation of the $143^{rd}$ amino acid residue of the wild-type haptoglobin sequence represented by SEQ. ID. NO: 1 or the physiologically equal protein. The physiologically equal protein can include a functional equivalent and a functional derivative that are functionally equal to the mutant haptoglobin protein which lost site specific cleavage capacity because of the mutation of the $143^{rd}$ amino acid residue.

The said "functional equivalent" indicates an amino acid sequence variant wherein a part or the whole amino acid sequence has been substituted or a part of amino acid has been deleted or added, but displays actually the same physiological activity as the mutant haptoglobin protein.

In addition, the present invention provides a composition for promoting angiogenesis comprising the polypeptide encoded by the mutant haptoglobin polynucleotide or the recombinant vector harboring the mutant haptoglobin gene.

The composition for promoting angiogenesis comprising the said polypeptide or the recombinant vector is characterized by the function of promoting tube formation and cell migration which favors angiogenesis. So, the composition for promoting angiogenesis of the present invention has the effect of preventing or treating angiogenesis-defect related diseases. Therefore, the present invention provides a composition comprising the polypeptide or the recombinant vector of the invention for the prevention or treatment of angiogenesis-defect related diseases.

The angiogenesis-defect related disease that can be prevented or treated by the composition for promoting angiogenesis of the present invention is selected from the group consisting of diabetic ulcer, gangrene, ischemic disease, occlusive vascular disease, cardiovascular disease, and local ischemia, but not always limited thereto.

The composition for promoting angiogenesis or the composition for the prevention or treatment of invention for the prevention or treatment of angiogenesis of the present invention can contain a pharmaceutically effective dose of the polypeptide or the recombinant vector alone as an active ingredient or can contain, in addition to the active ingredient, one or more pharmaceutically acceptable carriers, excipients, or diluents additionally.

In the above, "pharmaceutically effective dose" indicates the amount of the active ingredient that is enough to deliver a wanted physiological or pharmaceutical effect when it is administered to human or animals. However, the pharmaceutically effective dose herein can be adjusted according to age, weight, health condition, and gender of patient, administration pathway, and duration of treatment, etc.

In the above, "pharmaceutically acceptable" indicates the condition that when the target material is administered to human, it does not cause such general allergic reactions as gastroenteric trouble and dizziness or similar reactions to those. The carriers, excipients and diluents are exemplified by lactose, dextrose, sucrose, sorbitol, mannitol, xylitol, erythritol, maltitol, starch, acacia rubber, alginate, gelatin, calcium phosphate, calcium silcate, cellulose, methyl cellulose, microcrystalline cellulose, polyvinyl pyrrolidone, water, methylhydroxybenzoate, propylhydroxybenzoate, talc, magnesium stearate and mineral oil. In addition, fillers, antiaggregations, lubricants, wetting agents, flavors, emulsifiers, and antiseptics, can also be included.

The composition of the present invention can be formulated properly in a proper form by those in the art, in order for the active ingredient to be delivered fast, continuously, or delayed purposefully after administered to mammals. For example, the composition can be formulated in various formulas for oral- or parenteral administration.

The representative formulation for parenteral administration is injectable solutions, which are preferably exemplified by isotonic aqueous solutions or suspensions. The injectable solution can be prepared by using a proper dispersing agent, wetting agent, and suspending agent according to the conventional method well known to those in the art. For example, each ingredient is dissolved in saline or buffer to prepare injectable solutions. The formulation for oral administration is exemplified by oral tablets, buccal tablets, troches, capsules, elixirs, suspensions, syrups, and wafers. These formulations can additionally include, in addition to the active ingredient, diluents (for example, lactose, dextrose, sucrose, mannitol, sorbitol, cellulose, and/or glycine) and lubricants (for example, silica, talc, stearate and its magnesium or calcium salt, and/or polyethylene glycol). Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavors, and sweeteners can be additionally included thereto.

The composition of the present invention can additionally contain preservatives, wettable powders, emulsifiers, salts or buffers for the regulation of osmotic pressure, and other therapeutically useful materials, and the composition can be formulated by the conventional method.

The composition of the present invention can be administered via various pathways including oral administration, transdermal, hypodermic, intravenous, and intramuscular injection. The dose of the active ingredient can be adjusted according to the administration pathway, age, gender, and weight of patient, severity of disease, etc. The composition of the invention can be co-administered with any informed compound that can increase the targeting effect.

The composition of the present invention can be administered to human and animals via oral administration or parenteral administration including intravenous injection, hypodermic injection, intranasal administration and intraperitoneal injection. The oral administration herein includes sublingual administration. The parenteral administration herein includes hypodermic injection, intramuscular injection, intravenous injection, and dripping administration.

The effective dose of the polypeptide or the recombinant vector, the active ingredient of the composition of the invention, can be administered by single dose or by multiple dose of fractionated treatment protocol for a long term. The amount of the active ingredient in the composition of the present invention can vary from the severity of disease, but a preferable effective dose for an adult patient is 100 µg~3,000 mg, which can be administered for a few times a day. However, the effective dose of the physiologically active ingredient is generally determined by considering not only the administration pathway and administration times but also age, weight, health condition, gender, severity of disease, diet, and excretion. Therefore, those who have general knowledge of this field can determine the effective dose of the active ingredient according to a specific purpose, for example, for the prevention or treatment of angiogenesis-defect related disease. The composition of the present invention is not limited to a specific formulation, administration pathway, and administration method, as long as they do not change the effect of the invention.

Advantageous Effects

The composition for promoting angiogenesis comprising the recombinant vector introduced with the mutant haptoglobin polynucleotide or the mutant haptoglobin polypeptide of the present invention as an active ingredient is excellent in promoting the activity of angiogenesis so as to induce the differentiation of endothelial progenitor cells into mature endothelial cells, and is excellent in inducing capillary-like tube formation, and also is excellent in accelerating cell migration, so that it can be efficiently used for the treatment of disease caused by non-formation of blood vessels.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation and Separation of Mutant Haptoglobin

To prepare a haptoglobin having excellent angiogenesis promoting activity, the present inventors substituted the $143^{rd}$ amino acid Arg of the sequence of the wild-type haptoglobin represented by SEQ. ID. NO: 1 with Gln or Leu. As a result, the mutant haptoglobin (SEQ. ID. NO: 2 or SEQ. ID. NO: 3) was prepared. The preparation procedure for the mutant haptoglobin is described in more detail hereinafter.

<1-1> Preparation of Wild-Type Haptoglobin and Construction of Expression Vector Containing the Same Haptoglobin Hp2 cDNA of human cDNA library was amplified by using the following set of primers and Taq MasterMix (Qiagen) according to the manufacturer's instruction.

```
Hp2-F:
                                        (SEQ. ID. NO: 8)
5'-GCGAATTCGCCACCATGAGTGCCCTGGGAGCTG-3'

Hp2-R:
                                        (SEQ. ID. NO: 9)
5'-CCGGTACCGTTCTCAGCTATGGTCTTCTGAAC-3'
```

As a result, the expected fragment equivalent to 1218 by product was obtained. The amplified Hp2 cDNA was cloned into pcDNA 3.0 vector containing flag gene by using EcoRI and Kpnl. The vector constructed above was sequenced and confirmed to clone successfully with accurate direction and frame.

<1-2> Preparation of Mutant Haptoglobin and Construction of Expression Vector Containing the Same To substitute Arg, the $143^{rd}$ amino acid of the wild-type haptoglobin amino acid sequence represented by SEQ. ID. NO: 1, with Gln or Leu, the sequence CGG encoding Arg was mutated into CAG so as to encode Gln or into CTG so as to encode Leu (SEQ. ID. NO: 4 or SEQ. ID. NO: 5). At this time, QuickChange site-directed mutagenesis kit (Stratagene) was used for the mutation according to the manufacturer's instruction and the final mutant haptoglobin gene was cloned into pcDNA3.0 vector containing Flag gene.

```
Hp2-R143Q-F:
                                        (SEQ. ID. NO: 10)
5'-GCAAACCCAGTGCAGCAGATCCTGGGTGGACAC-3'

Hp2-R143Q-R:
                                        (SEQ. ID. NO: 11)
5'-GTGTCCACCCAGGATCTGCTGCACTGGGTTTGC-3'

Hp2-R143L-F:
                                        (SEQ. ID. NO: 12)
5'-GCAAACCCAGTGCAGCTGATCCTGGGTGGACAC-3'

Hp2-R143L-R:
                                        (SEQ. ID. NO: 13)
5'-GTGTCCACCCAGGATCAGCTGCACTGGGTTTGC-3'
```

The vector comprising the mutant haptoglobin gene was sequenced and confirmed to clone successfully with accurate direction and frame.

<1-3> Examination of the Expression of Wild-Type Haptoglobin and Mutant Haptoglobin by Western Blotting Cos7 cell line was transfected with the vector constructed in Example <1-1> or Example <1-2>. Particularly, cos7 cells were distributed in a 6-well plate at the density of $1 \times 10^6$ cells/well, followed by overnight culture. Then, the cells were transfected with the vector by using Lifopectamine™ (Invitrogen, USA) according to the manufacturer's instruction.

48 hours after the culture, 5× reducing sample buffer was loaded in the cell culture medium, followed by boiling. SDS-PAGE was performed and the protein was transferred onto PVDF membrane. The PVDF membrane was blocked by using blocking solution (5% skim milk) at room temperature for 1 hour, followed by reaction with rabbit anti-human Hp α antibody (1:500) or rabbit anti-human Hp β antibody (1:500) at room temperature for 2 hours. The PVDF membrane was washed with PBS three times for 10 minutes, followed by reaction with HRP-conjugated anti-rabbit IgG antibody (1:4000, Sigma) at room temperature for 1 hour.

Figure 4B:
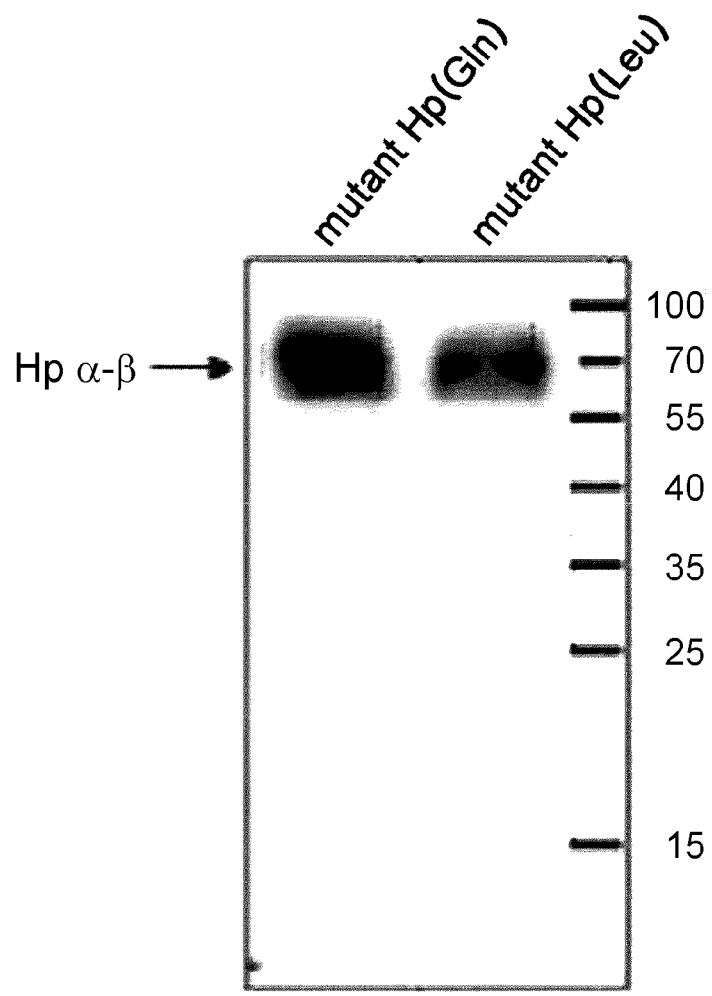

As a result, 20 kDa α chain (SEQ. ID. NO: 6) and 47 kDa β chain (SEQ. ID. NO: 7) were confirmed in the wild-type haptoglobin (Hp2-2) (FIGS. 4a and 4b), while 67 kDa band wherein α chain and β chain were linked was observed in the mutant haptoglobin wherein the $143^{rd}$ amino acid Arg was substituted with Gln (mutant Hp(Gln), SEQ. ID. NO: 2) (FIGS. 4a and 4b). In the meantime, 67 kDa band without digestion was also observed in another mutant haptoglobin (mutant Hp(Leu), SEQ. ID. NO: 3) having the replacement of the $143^{rd}$ amino acid Arg with Leu (FIG. 4c).

<1-4> Purification of Mutant Haptoglobin

To investigate the angiogenesis promoting effect of the mutant haptoglobin, the present inventors first purified the mutant haptoglobin. To do so, cos7 cell line was transfected with the recombinant vector by the same manner as described in Example <1-3>. 48 hours after the transfection, the cell culture medium was concentrated by using a centrifuge and then passed through a filter. The cell culture medium was diluted with TBS (5×), which was loaded in Anti-FLAG M2 affinity gel (Sigma). The gel was applied to Anti-FLAG column by using HiLoad Pump-P50 (Pharmaciabiotech). Elution was performed by using FLAG peptide (Sigma) according to the manufacturer's instruction. After being through SDS-PAGE, the eluent proceeded to Western blotting by using Anti-flag monoclonal antibody to investigate the expression of haptoglobin. The eluted haptoglobin was quantified by ELISA and stored at –70° C. (1 μg/ml).

Example 2

Observation of VEGF and VEGFR2 Expressions According to the Treatment of Wild-Type Haptoglobin and Mutant Haptoglobin: qRT-PCR In the signal transduction system involved in blood vessel system, VEGF/VEGFR2 pathway is a major growth factor signaling pathway that regulates the proliferation, chemotactic migration, and survival of VECs. The expressions of VEGF and VEGFR2 were known to be increased during angiogenesis. So, the present inventors investigated the expressions of VEGF and VEGFR2 by quantitative RT-PCR in order to examine whether or not the mutant haptoglobin had the better angiogenesis promoting effect than the wild-type haptoglobin.

To do so, the present inventors distributed HUVEC cells in a 24-well plate at the density of $1 \times 10^5$ cells/well, followed by overnight culture. Then, the cells were treated with the wild-type haptoglobin (Hp 2-2, 1 μg/ml) or the mutant haptoglobin (0.1 μg/ml), followed by additional culture for 24 hours. Quantitative RT-PCR was performed to measure the expressions of VEGF and VEGFR2. At this time, RT-PCR was performed by the conventional procedure. Particularly, quantitative real-time PCR was performed by using a PCR machine (MX-3000P; Stratagene) with FullVelocity SYBR Green QPCR master mix (Stratagene, La Jolla, Calif.). The sets of primers used for this PCR were as follows.

```
VEGF-F:
                                        (SEQ. ID. NO: 14)
5'-GCGGAGAAAGCATTTGTTTGT-3'
```

-continued

VEGF-R:
(SEQ. ID. NO: 15)
5'-TTGCAGATGTGACAAGCCG-3'

VEGFR2-F:
(SEQ. ID. NO: 16)
5'-TGGGAACCGGAACCTCACTATC-3'

VEGFR2-R:
(SEQ. ID. NO: 17)
5'-GTCTTTTCCTGGGCACCTTCTATT-3'

GAPDH-F:
(SEQ. ID. NO: 18)
5'-ACCACAGTCCATGCCATCAC-3'

GAPDH-R:
(SEQ. ID. NO: 19)
5'-TCCACCACCCTGTTGCTGTA-3'

As a result, as shown in FIGS. 5a and 5b, when the cells were treated with the mutant haptoglobin (Hp(Gln) or Hp(Leu)) at the concentration of 0.1 μg/ml, the mRNA levels of VEGF and VEGFR2 were 2~3 times increased compared with the control (treated with PBS). In the meantime, in the cells treated with the wild-type haptoglobin (Hp 2-2), the expressions of VEGF and VEGFR2 were not much changed at the concentration of either 0.1 μg/ml (data not shown) or 1 μg/ml, compared with the control.

Example 3

Comparison of Tube Formation According to the Treatment of Wild-Type Haptoglobin and Mutant Haptoglobin To investigate the angiogenesis related effect of the wild-type haptoglobin and the mutant haptoglobin, the present inventors observed in vitro tube formation on Matrigel by the wild-type haptoglobin and the mutant haptoglobin.

Particularly, cold Matrigel (BD Biosciences, San Jose, Calif.) was placed in each well of a 48-well plate, followed by polymerization at 37° C. for 30 minutes. HUVEC cells treated with the wild-type haptoglobin (Hp 2-2, 1 μg/ml) or the mutant haptoglobin (Hp(Gln), Hp(Leu) 0.1 μg/ml) were distributed on the Matrigel ($4 \times 10^4$ cells/well), followed by culture in EGM-2 medium supplemented with 0.5% FBS for 6 hours. Then, the tubular network formation was observed under microscope.

As a result, in the cells treated with the wild-type haptoglobin (Hp 2-2) at the concentration of 1 μg/ml, capillary-like tube formation was not much different from that in the control cells (treated with PBS). In the cells treated with the mutant haptoglobin (Hp(Gln), Hp(Leu)) at the concentration of 0.1 μg/ml, capillary-like tube formation was significantly promoted (FIG. 6). Therefore, it was confirmed that the mutant haptoglobin was more effective in inducing tubular network formation than the wild-type haptoglobin.

Example 4

Comparison of Cell Migration According to the Treatment of Wild-Type Haptoglobin and Mutant Haptoglobin To investigate whether or not the wild-type haptoglobin and the mutant haptoglobin could affect the functions of endothelial cells, migration assay was performed after the treatment of the wild-type haptoglobin and the mutant haptoglobin.

Particularly, the following experiment was performed by using Oris™ cell migration assay kit according to the manufacturer's instruction. HUVEC cells were distributed in a collagen I coated 96 well plate at the density of $5 \times 10^4$ cells/well, followed by overnight culture. The cells were treated with the wild-type haptoglobin (Hp 2-2, 1 μg/ml) or the mutant haptoglobin (Hp(Gln), Hp(Leu) 0.1 μg/ml), followed by culture for 24 hours. Photographs were taken under microscope and then the distance of cell migration was measured. The migration distance was measured at randomly selected 12 spots and the results were presented as mean±standard error.

As a result, when the mutant haptoglobin (Hp(Gln), Hp(Leu)) was treated to the cells, the migration distance was significantly increased, compared with the cells treated with the wild-type haptoglobin (Hp 2-2) and the control cells treated with PBS (FIG. 7a~FIG. 7c).

Example 5

Statistical Analysis

To analyze the difference in the results obtained from the experimental groups and the control groups, student's t-test and variance one way analysis were performed. When P<0.05, it was considered as statistically significant.

From the above results, it was confirmed that the mutant haptoglobin accelerated angiogenesis of vascular endothelial cells, particularly it displayed significant angiogenesis promoting effect at as low concentration as 0.1 μg/ml. Compared with the wild-type haptoglobin which has been known to have angiogenesis inducing effect at the concentration of at least 20 μg/ml, the mutant haptoglobin could be considered as an improved material that displayed higher activity of promoting angiogenesis.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A mutant haptoglobin polypeptide composed of the amino acid sequence wherein the 143$^{rd}$ amino acid of the sequence represented by SEQ ID NO: 1, is substituted with amino acid other than Arg.

2. The mutant haptoglobin polypeptide according to claim 1, wherein the mutant haptoglobin is characterized by the inhibition of the site-specific cleavage of the 143$^{rd}$ amino acid of the sequence represented by SEQ ID NO: 1.

3. The mutant haptoglobin polypeptide according to claim 1, wherein the mutant haptoglobin is characterized by having the amino acid sequence represented by SEQ ID NO: 2 wherein Arg, the 143$^{rd}$ amino acid of the sequence represented by SEQ ID NO: 1, is substituted with Gln.

4. The mutant haptoglobin polypeptide according to claim 1, wherein the mutant haptoglobin is characterized by having the amino acid sequence represented by SEQ ID NO: 3 wherein Arg, the 143$^{rd}$ amino acid of the sequence represented by SEQ ID NO: 1, is substituted with Leu.

5. A polynucleotide encoding the mutant haptoglobin polypeptide of claim 1.

6. The polynucleotide according to claim 5, wherein the polynucleotide is composed of the nucleotide sequence represented by SEQ ID NO: 4 or SEQ ID NO: 5.

7. A recombinant vector comprising the polynucleotide of claim 5.

8. A transformant transfected with the recombinant vector of claim 7.

9. A composition for accelerating angiogenesis comprising one or more components selected from the group consisting of the mutant haptoglobin polypeptide of claim 1, the recombinant vector containing the polynucleotide encoding the mutant haptoglobin polypeptide, and the transformant transfected with the said recombinant vector.

10. A pharmaceutical composition for the prevention or treatment of angiogenesis-defect related disease comprising one or more components selected from the group consisting of the mutant haptoglobin polypeptide of claim 1, the recombinant vector containing the polynucleotide encoding the mutant haptoglobin polypeptide, and the transformant transfected with the said recombinant vector, wherein the disease is selected from the group consisting of diabetic ulcer, gangrene, ischemic diseases, occlusive vascular diseases, cardiovascular diseases, and local ischemia.

* * * * *